US011311349B2

(12) United States Patent
Sweeney

(10) Patent No.: US 11,311,349 B2
(45) Date of Patent: Apr. 26, 2022

(54) INTEGRATED SURGICAL IMPLANT DELIVERY SYSTEM AND METHOD

(71) Applicant: Spinal Generations, LLC, Mokena, IL (US)

(72) Inventor: Patrick J. Sweeney, Flossmoor, IL (US)

(73) Assignee: Spinal Generations, LLC, Mokena, IL (US)

( * ) Notice: Subject to any disclaimer, the term of this patent is extended or adjusted under 35 U.S.C. 154(b) by 0 days.

(21) Appl. No.: 17/068,382

(22) Filed: Oct. 12, 2020

(65) Prior Publication Data

US 2021/0030514 A1 Feb. 4, 2021

Related U.S. Application Data

(60) Continuation of application No. 15/810,966, filed on Nov. 13, 2017, now Pat. No. 10,799,318, which is a
(Continued)

(51) Int. Cl.
*A61B 90/98* (2016.01)
*G06Q 10/08* (2012.01)
*G16H 40/63* (2018.01)
*G16H 40/20* (2018.01)
*A61B 90/96* (2016.01)
*G16Z 99/00* (2019.01)
(Continued)

(52) U.S. Cl.
CPC ............ *A61B 90/98* (2016.02); *A61B 90/90* (2016.02); *A61B 90/96* (2016.02); *G06Q 10/083* (2013.01); *G06Q 10/087* (2013.01); *G16H 40/20* (2018.01); *G16H 40/63* (2018.01); *G16Z 99/00* (2019.02); *A61B 2034/256* (2016.02)

(58) Field of Classification Search
CPC ......... A61B 90/98; A61B 90/90; A61B 90/96; A61B 2034/256; G16Z 99/00; G16H 40/63; G16H 40/20; G16H 20/40; G06Q 10/087; G06Q 10/083
USPC .......................................................... 705/28
See application file for complete search history.

(56) References Cited

U.S. PATENT DOCUMENTS 7,492,257 B2   2/2009   Tethrake et al.
7,492,261 B2   2/2009   Cambre et al.
(Continued)

FOREIGN PATENT DOCUMENTS

CN   102047256 A   5/2011
CN   102760240 A   10/2012

OTHER PUBLICATIONS

International Search Report and Written Opinion on PCT/US2016/064932, dated Feb. 1, 2017, 9 pages.

*Primary Examiner* — Garcia Ade
(74) *Attorney, Agent, or Firm* — Foley & Lardner LLP

(57) ABSTRACT

An operating room display system includes a display device, a sensor coupled to the display device and configured to detect a presence of a medical device disposed within the operating room, a communications interface communicatively coupled to the display device and the sensor, and a memory communicably coupled to the communications interface, wherein the memory comprises a device information module. The display device is configured to show a display providing information from the device information module to a user in the operating room regarding the medical device detected by the sensor.

20 Claims, 9 Drawing Sheets

Related U.S. Application Data division of application No. 14/088,069, filed on Nov. 22, 2013, now Pat. No. 9,827,048.

(51) Int. Cl.
    *A61B 90/90*     (2016.01)
    *A61B 34/00*     (2016.01)

(56) References Cited

U.S. PATENT DOCUMENTS

| | | |
|---|---|---|
| 9,301,845 B2 | 4/2016 | Bonutti |
| 2005/0062603 A1 | 3/2005 | Fuerst et al. |
| 2006/0027662 A1 | 2/2006 | Baradi |
| 2006/0145856 A1 | 7/2006 | Tethrake et al. |
| 2006/0236373 A1 | 10/2006 | Graves et al. |
| 2008/0030345 A1* | 2/2008 | Austin .................. A61B 90/98 340/572.8 |
| 2008/0252459 A1* | 10/2008 | Butler ................ G06K 7/10366 340/572.1 |
| 2008/0266131 A1* | 10/2008 | Richardson ............. G01S 19/48 340/4.62 |
| 2009/0091453 A1 | 4/2009 | Ishida et al. |
| 2009/0102653 A1* | 4/2009 | McGinnis ............... E05B 45/06 340/551 |
| 2010/0161345 A1* | 6/2010 | Cain ...................... G06Q 10/08 705/2 |
| 2011/0007950 A1 | 1/2011 | Deutsch |
| 2012/0296381 A1 | 11/2012 | Matos |
| 2012/0298381 A1 | 11/2012 | Taylor |
| 2013/0066647 A1 | 3/2013 | Andrie et al. |
| 2013/0091679 A1 | 4/2013 | Gloger et al. |
| 2013/0328661 A1 | 12/2013 | Phillips et al. |
| 2013/0329661 A1 | 12/2013 | Chen et al. |
| 2014/0263674 A1 | 9/2014 | Cerveny |
| 2015/0061834 A1 | 3/2015 | Khoury |
| 2016/0085922 A1 | 3/2016 | Sweeney |

\* cited by examiner

INTEGRATED SURGICAL IMPLANT DELIVERY SYSTEM AND METHOD

CROSS-REFERENCE TO RELATED APPLICATIONS

This application is a continuation of U.S. application Ser. No. 15/810,966, filed Nov. 13, 2017, which is a divisional of U.S. application Ser. No. 14/088,069, filed Nov. 22, 2013, each of which is incorporated herein by reference in its entirety.

BACKGROUND

Traditional systems and methods for providing support for a surgical operation that involves a medical device (e.g., an implant to be inserted in the surgery, a tool used in the surgery, etc.) typically include pre-operation planning, providing support during the operation, and post-operation support. A product specialist for the medical device may provide such support for the use of the medical device throughout the surgical operation process.

The product specialist may provide various functions for a hospital relating to the medical device. The product specialist may be on-site to provide the various functions. For example, the on-site product specialist may provide the surgical staff support and training for using the medical device in a procedure (e.g., how to insert an implant into a patient, how to use one or more tools during a surgical operation, etc.). The on-site product specialist may also provide advisory services to a doctor relating to the use of the medical device. Further, the on-site product specialist may track inventory of the medical device in the hospital and provide sales-related services. For example, the on-site product specialist may order more medical devices for the hospital, create an invoice charging the hospital for use of the medical device, etc.

SUMMARY

One embodiment of the present disclosure relates to a medical device inventory tracking system. The system includes a shipping container configured to contain a medical device. The system further includes a sensor coupled to the shipping container and configured to detect the presence of the medical device. The system further includes a processing circuit integrated into the shipping container. The processing circuit is configured to receive a signal from the sensor and to perform an action based upon the signal.

Another embodiment of the present disclosure relates to a system for monitoring a surgical procedure using a medical device in an operating room. The system includes a camera positioned in the operating room. The system further includes a display positioned in the operating room. The system further includes a telecommunications interface configured to permit a videoconference between personnel in the operating room and a product specialist associated with the medical device using the display and the camera.

Yet another embodiment of the present disclosure relates to a method for providing support to a surgical team conducting a procedure involving a medical device. The method includes providing a camera and a display. The method further includes establishing a video connection between the operating room and a product specialist, wherein video of the product specialist is provided on the display. The method further includes using the camera to provide video to the product specialist.

Alternative exemplary embodiments relate to other features and combinations of features as may be generally recited in the claims.

BRIEF DESCRIPTION OF THE FIGURES

The disclosure will become more fully understood from the following detailed description, taken in conjunction with the accompanying figures, wherein like reference numerals refer to like elements, in which.

DETAILED DESCRIPTION

Figure 1:
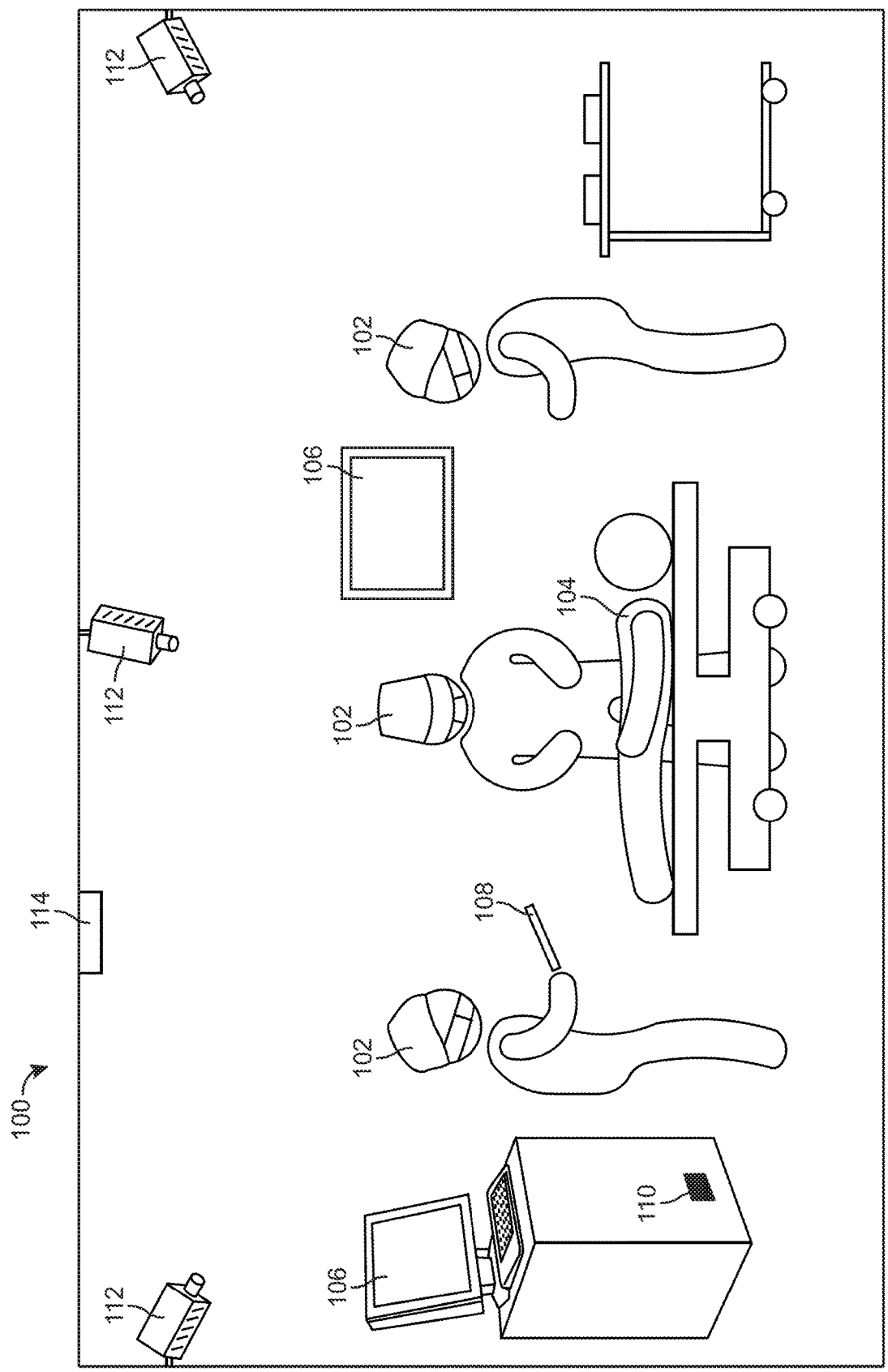
FIG. 1 is an illustration of an operating room in which the systems and methods described herein may be implemented, according to an exemplary embodiment.

Referring generally to the figures, systems and methods for tracking medical device use and providing services related to the medical device are shown and described. The systems and methods described herein may be used in place of having an on-site product specialist. The systems and methods described herein may be used to track the use and inventory of medical devices in a hospital, to set up simulcasts or videoconferences with a product specialist located remotely from the hospital, and to assist personnel in an operating room. The systems and methods allow a product specialist to assist with use of a medical device, but in an off-site manner instead of being on-site.

In one embodiment, a system for monitoring a surgical procedure using a medical device in an operating room is described. The system includes one or more cameras positioned in the operating room, and one or more displays (e.g., monitors) positioned in the operating room. The system includes a telecommunications link configured to permit a videoconference between personnel in the operating room (e.g., surgeons) and a product specialist (or other person) associated with the medical device. The videoconference is provided using the one or more displays to present the product specialist to the surgeon and the one or more cameras for providing the product specialist with a view of the operating room, including the patient, medical device, etc.

The monitoring system further includes a module for identifying the medical device, either by optical scanning by the cameras, image recognition, or an RFID reader configured to scan a RFID tag of the medical device. The monitoring system then identifies the product specialist associated with the medical device along with other medical device information. Further, the monitoring system tracks usage of the medical device and performs various functions such as updating an inventory of the medical device, generating an invoice for the medical device being used, and generating an order to provide to a vendor, supplier, distributor, etc. for re-stocking the hospital with the medical device.

In another embodiment, a medical device inventory tracking system is described. The system includes a shipping container configured to contain one or more medical devices. The system further includes a sensor coupled to the shipping container configured to detect the presence of the medical devices. The system further includes a processing circuit integrated into the shipping container, configured to receive a signal from the sensor when a medical device is taken and used, and to perform an action based on the signal. The action may be updating an inventory, generating an invoice, generating an order to provide to a vendor for re-stocking the hospital with the medical device, or otherwise.

The medical device inventory tracking system includes a module for identifying the medical device based on the signal from the sensor. In one embodiment, the sensor is an RFID reader configured to scan an RFID tag of the medical device. The tracking system may then perform various functions such as updating an inventory of the medical device in the shipping container, generating an invoice for the medical device being used, and generating an order to provide to a vendor, supplier, distributor, etc. for re-stocking the hospital with the medical device.

The monitoring system and tracking system as presented in the present disclosure may be used to provide various services to the hospital. In one embodiment, one of the monitoring system and tracking system may be provided for monitoring medical device usage. In another embodiment, the hospital may include both a monitoring system in an operating room and a tracking system integrated with a shipping container to monitor medical device usage, and the monitoring system and tracking system may work in concert. In yet another embodiment, the monitoring system and tracking system may be implemented as a single system in the hospital. In yet other embodiments, some of the functionality of the monitoring system as described below may be executed in the tracking system, and vice versa. It should be understood that any such combination of functionality of the monitoring system and tracking system described above fall within the scope of the present disclosure.

Referring to FIG. 1, an illustration of an operating room 100 in which the systems and methods described herein may be implemented is shown, according to an exemplary embodiment. Operating room 100 may generally be an environment in which a surgical procedure is performed. While the systems and methods described herein are described as implemented in an operating room of a hospital, it should be understood that in other exemplary embodiments, the systems and methods described herein may be implemented in any other location.

Operating room 100 may be occupied by one or more surgeons 102 (e.g., a surgical team, or other personnel) and a patient 104. Operating room 100 may include various equipment for assisting surgeons 102 with a surgical operation to be performed on patient 104. For example, operating room 100 includes displays 106. Displays 106 may be configured to display information, to provide video, or otherwise. For example, a surgeon 102 may participate in a videoconference with a product specialist located remotely from operating room 100 via displays 106. As another example, a surgeon 102 may view information related to a medical device being used in an operation on displays 106.

In one embodiment, displays 106 may be in various fixed locations in operating room 100. For example, one display 106 is shown mounted on a wall of operating room 100, and another display 106 is shown on a table and may be connected to a computer including a processing circuit configured to control display 106. In other embodiments, displays 106 may be temporarily or permanently positioned in operating room 100 by a surgeon 102 in any location (e.g., mounted or anchored to an instrument table, anchored in a position that allows the surgeon to view the display while operating, etc.). Displays 106 may be displays of any type of configuration (e.g., LCD, CRT display, etc.).

Operating room 100 may further include one or more remote devices 108. Remote devices 108 may be devices belonging to a surgeon 102 or may be associated with operating room 100. Remote devices 108 may be, for example, cell phones, tablets, laptop computers, or other handheld devices. Remote devices 108 may be configured to display information in a similar manner to displays 106. For example, a remote device 108 such as a tablet may be used in a videoconference. Remote devices 108 may further be configured to provide support to surgeons 102 during an operation. Remote devices 108 may be held by a surgeon 102 or mounted in an advantageous location for viewing by surgeons 102.

While not shown in FIG. 1, the operating room 100 environment may further include other devices for providing sensory feedback to surgeons 102. For example, operating room 100 may include speakers for providing auditory feedback (e.g., from a product specialist communicating remotely with surgeons 102). As another example, one or more surgeons may have an earpiece, microphone, headset, or other devices useful for communications with a product specialist without being near a display 106 or remote device 108.

Operating room 100 is shown to include a monitoring system 110 which may be implemented in a computing device located in operating room 100 (or located remotely from operating room 100). Monitoring system 110 may generally be configured to monitor the activity in operating room 100. In the present embodiment, monitoring system 110 is configured to monitor the use of one or more medical devices during an operation. For example, monitoring system 110 may be able to detect when a medical device is being used or about to be used in an operation. Monitoring system 110 may identify the medical device and provide support in response, such as providing surgeons 102 with medical device details, setting up a videoconference or simulcast, or otherwise. As shown in FIG. 1, monitoring system 110 may be executed in a computer connected to a display 106, in other embodiments, monitoring system 110 may be in any type of computing device local or remotely located from operating room 100. The operation of monitoring system 110 is described in greater detail in FIG. 4.

Operating room 100 is further shown to include a plurality of cameras 112. Cameras 112 may be configured to provide visual support during an operation in operating room 100. For example, cameras 112 may record video to be provided in a simulcast of an operation for a product specialist. As another example, video or images captured by cameras 112 may be used to detect or verify the use of a medical device in an operation. Cameras 112 may further provide general monitoring services for operating room 100 and the hospital. Input from cameras 112 may be received at monitoring system 110.

In addition to cameras 112, one or more webcams or remote devices 108 may further be configured to provide monitoring services for operating room 100. While the present disclosure describes monitoring activities using cameras 112, it should be understood that other devices with video capabilities (e.g., webcams, cell phones, tablets, etc.) may be used to provide monitoring services in addition to or in lieu of cameras 112.

Figure 2:
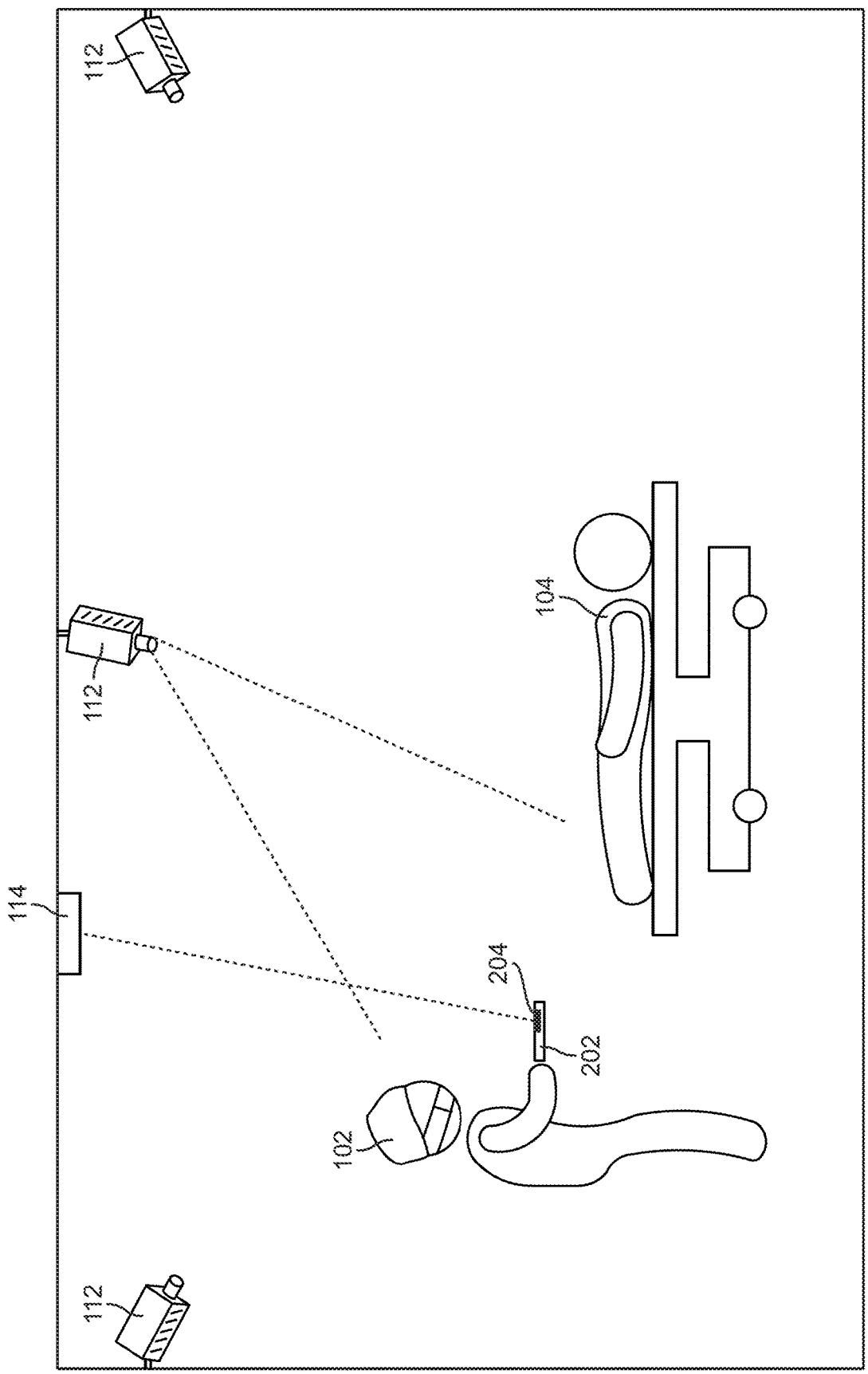
FIG. 2 is an illustration of an operating room including cameras and sensors for detecting a medical device, according to an exemplary embodiment.

Operating room 100 is further shown to include an RFID reader 114 configured to detect an RFID tag. Referring also to FIG. 2, the detection of a medical device using cameras 112 and RFID reader 114 in operating room 100 is illustrated. Surgeon 102 is shown holding a medical device 202. Medical device 202 may be an implant, a tool, or the like. Medical device 202 includes an RFID tag 204 which may be detected by RFID reader 114. RFID reader 114 may be located in any position in operating room 100 such that a medical device including an RFID tag to be used in an operation is detected. For example, RFID reader 114 may be located in a ceiling, wall, or floor of operating room 100, may be coupled to a computer, monitor, operating table, or any other equipment in operating room 100, may be in a remote device 108 of a surgeon 102, or otherwise. In various embodiments, RFID reader 114 may be automatically configured to scan for and detect medical devices, or a surgeon 102 may approach RFID reader 114 to manually scan the medical device. In one embodiment, operating room 100 may include other sensors in addition to or in place of RFID reader 114 for sensing the presence of medical device 202.

Cameras 112 may be used instead of or in concert with RFID reader 114 to identify medical device 202. For example, if medical device 202 includes a bar code, cameras 112 may be configured to capture video or images of the bar code, and a processing circuit associated with cameras 112 (e.g., monitoring system 110) may read the bar code to identify the medical device. As another example, cameras 112 may capture images of medical device 202 and a processing circuit associated with cameras 112 (e.g., monitoring system 110) may use object recognition to identify medical device 202 without the use of an identifier associated with medical device 202. Surgeon 102 may approach a camera 112 to have the camera record an image or video of the medical device, or cameras 112 may be configured to automatically record an image or video, and monitoring system 110 may identify the device.

Figure 3:
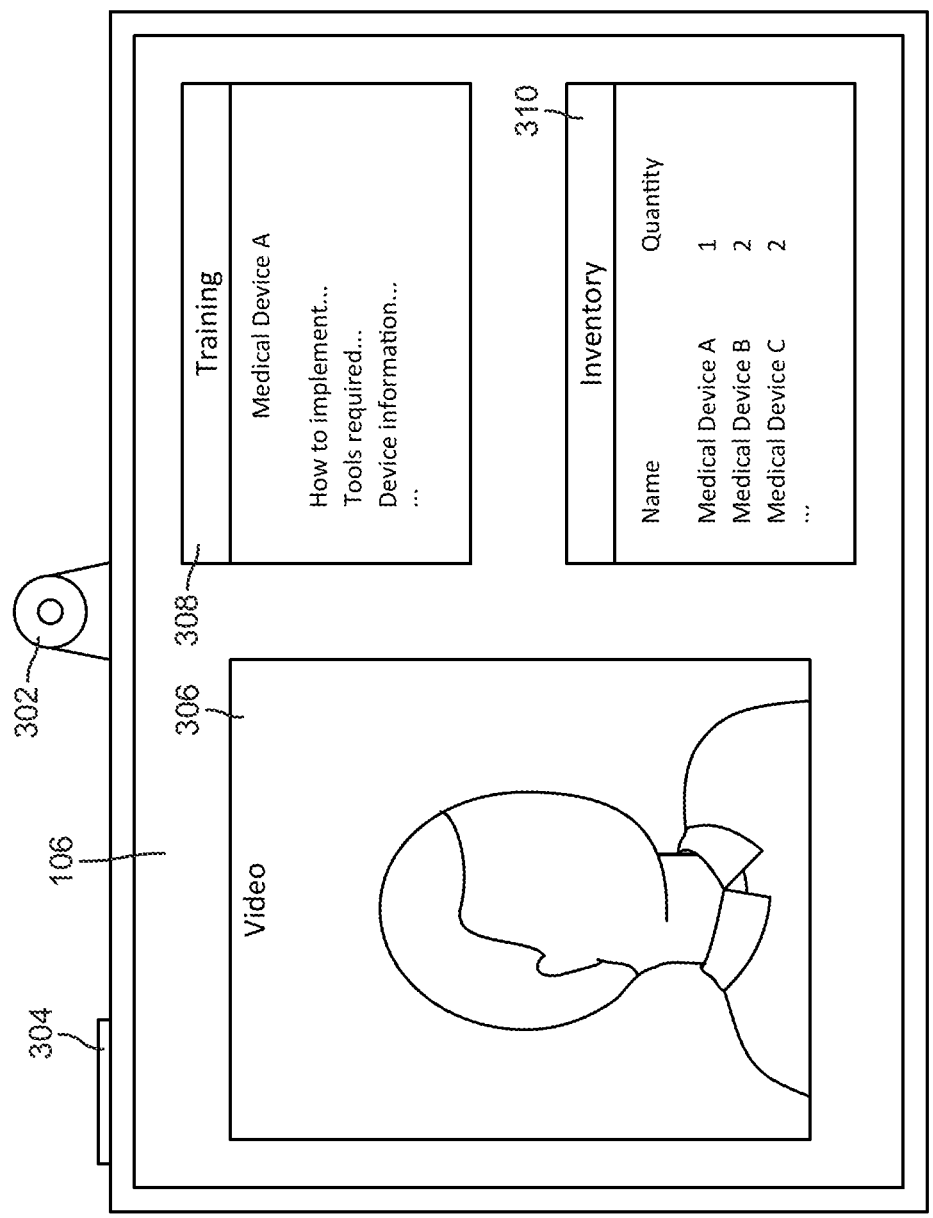
FIG. 3 is an example display for providing a video connection between personnel in an operating room and a product specialist, according to an exemplary embodiment.

Referring now to FIG. 3, an example display 106 for providing a video connection between personnel in an operating room and a product specialist is shown, according to an exemplary embodiment. Display 106 may be used by a surgeon or other personnel to communicate with a product specialist and to view information related to an operation or medical device. In the embodiment of FIG. 3, display 106 is described with respect to providing video and information relating to a medical device, but display 106 may additionally include other information relevant to the personnel that is not related directly to the medical device.

Display 106 may be connected to a camera 302 and sensor 304. Camera 302 and sensor 304 may be coupled to display 106. Camera 302 may be, for example, a webcam that feeds video or images to a viewer (e.g., a product specialist) located remotely from operating room 100. Camera 302 may be used to provide a simulcast of the operation or of one or more surgeons or other personnel. In other embodiments, there may not be a camera 302 local to display 106 and the video feed or images from one or more of cameras 112 may be provided, or video from both cameras 112 and camera 302 may be provided. Sensor 304 may be a configured to detect a medical device and may have a functionality similar to RFID reader 114 as described above. In various embodiments, there may not be a sensor 304 local to display 106, or sensor 304 may be used in place of RFID reader 114.

Display 106 is shown to include a video 306 portion that allows a surgeon to communicate face-to-face with a product specialist. Video 306 portion may include a live stream of the product specialist. Video 306 portion may alternatively or additionally be used to show a tutorial or other instruction for using a medical device in an operation.

Display 106 is further shown to include other portions for providing medical device information. For example, display 106 may include a training 308 section, where the surgeon may view medical device information, instructions for using the medical device in an operation, other tools needed or requirements for using the medical device, etc. Display 106 may also include an inventory 310 section, where the surgeon may view inventory-related information (e.g., how many medical devices are in stock in the hospital, what medical devices are needed for the current operation, etc.). Display 106 may further include other sections to provide information to the personnel. For example, inventory 310 section may include information about an order to be placed to a vendor, distributor, supplier, etc. for replenishing a stock of a medical device in the hospital, an invoice charging the hospital for use of a medical device, or otherwise. As another example, display 106 may display information provided by a product specialist.

It should be understood that while display 106 is shown as presenting various information relating to the medical device, some or all of the features provided by display 106 may be alternatively or additionally provided on other devices. For example, some or all of the features of display 106 may be provided on a remote device 108 of a surgeon. Any number of displays and/or remote devices may be used in combination in operating room 100 to provide the features described herein.

While display 106 is described with reference to being provided in an operating room 100, it should be understood that a similar display may be provided for an off-site product specialist. The display may provide the product specialist with a live view of operating room 100 and the operation, along with inventory information of the hospital, medical device information, and other relevant information. The product specialist can then provide guidance for use of the medical device and for the operation.

Figure 4:
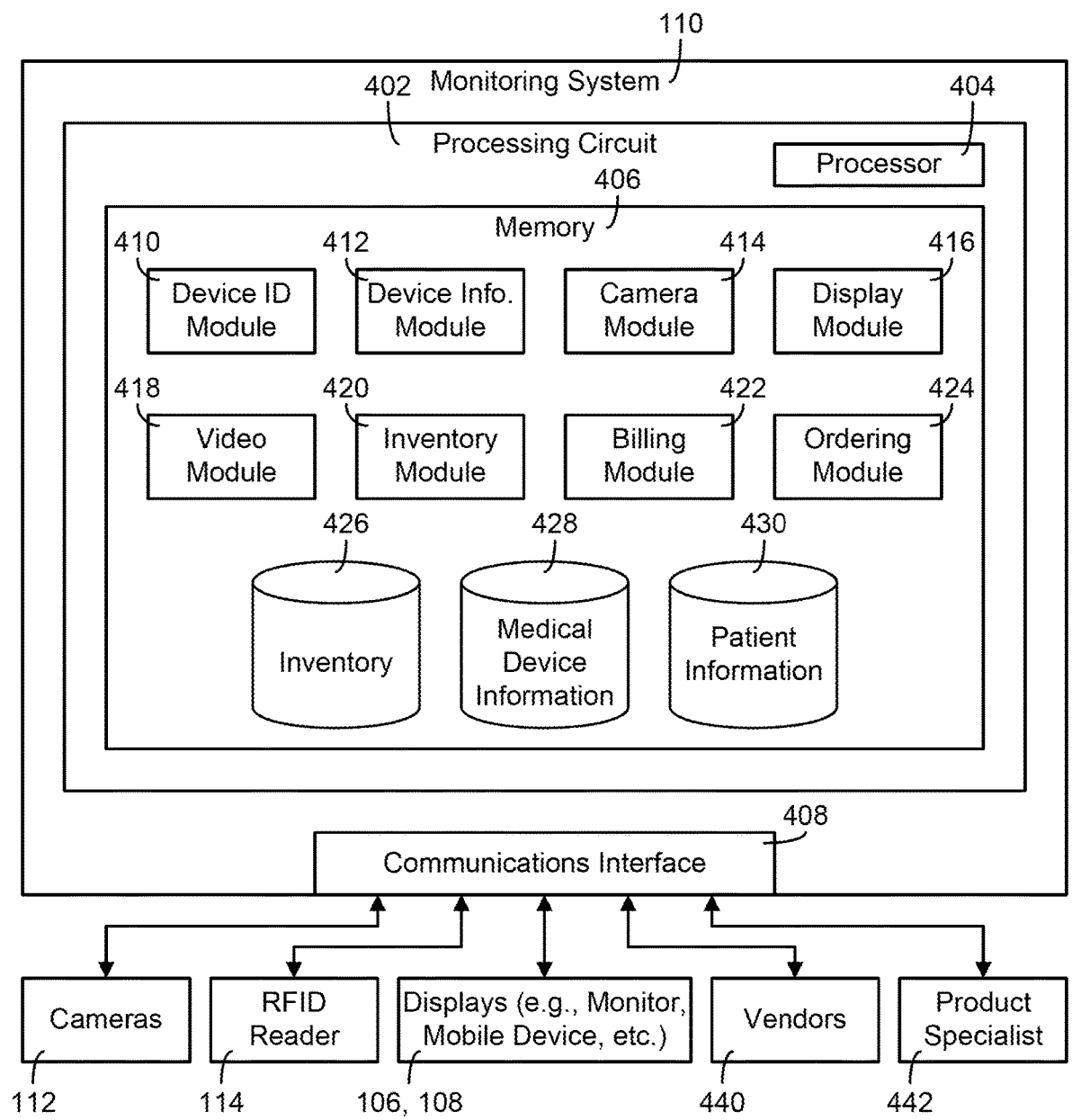
FIG. 4 is a block diagram of a monitoring system integrated into the operating room of FIG. 1 for tracking use of a medical device, according to an exemplary embodiment.

Referring now to FIG. 4, monitoring system 110 is shown in greater detail. Monitoring system 110 may generally be configured to monitor activity in an operating room, including the use of one or more medical devices in the operating room. For example, monitoring system 110 may identify a medical device 202, set up a videoconference or simulcast in operating room 100, update inventory, order and re-stock the medical device, and provide other such services.

As shown in FIG. 1, monitoring system 110 may be implemented in a computing system local to operating room 100; in other embodiments, monitoring system 110 may be located remotely from monitoring system 110. Further, while monitoring system 110 is shown as a single system, it should be understood that some of the modules, databases, and other components of monitoring system 110 may be located in different locations, computing devices, etc. (e.g., tracking system 900 as described below).

Monitoring system 110 is shown to include a communications interface 408 configured to communicate with various equipment, devices, and the like. Communications interface 408 may be configured to establish a wireless or wired (e.g., USB) connection with any number of devices that may provide input for monitoring system 110. For example, communications interface 408 may establish a connection with one or more cameras 112, RFID readers 114, various displays (e.g., displays 106 or remote device 108), sensors, and other devices in operating room 100. Communications interface 408 may further establish a connection with one or more vendors 440 (e.g., a medical device provider or distributor) and one or more product specialists 442. Product specialists 442 may be personnel trained and verified to provide medical support relating to a medical device. Product specialists 442 may be associated with one or more vendors, may be trained and funded by one or more vendors, or may otherwise be associated with the vendors in any way.

While communications interface 408 is shown as a single interface, it should be understood that monitoring system 110 may include a plurality of interfaces for communicating with a plurality of devices. For example, communications interface 408 may include a first interface configured to establish a wired or local connection with cameras 112 and RFID reader 114, and a second interface configured to establish a connection over a network with vendors 440 or product specialist 442.

Monitoring system 110 is shown to include a processing circuit 402 including a processor 404 and memory 406. Processor 404 may be implemented as a general purpose processor, an application specific integrated circuit (ASIC), one or more field programmable gate arrays (FPGAs), a group of processing components, or other suitable electronic processing components. Memory 406 is one or more devices (e.g., RAM, ROM, flash memory, hard disk storage, etc.) for storing data and/or computer code for completing and/or facilitating the various user or client processes, layers, and modules described in the present disclosure. Memory 406 may be or include volatile memory or non-volatile memory. Memory 406 may include database components, object code components, script components, or any other type of information structure for supporting the various activities and information structures of the present disclosure. Memory 406 is communicably connected to processor 404 and includes computer code or instruction modules for executing one or more processes described herein. Memory 406 is shown to include various modules 410-426 for completing the activities described herein.

Memory 406 is shown to include a device ID module 410. Device ID module 410 is configured to identify a medical device based on input from cameras 112, RFID reader 114, or other devices. In one embodiment, device ID module 410 may be configured to receive a signal from RFID reader 114. RFID reader 114 may detect the medical device via an RFID tag on the medical device, and an indication may be provided to device ID module 410.

In one embodiment, device ID module 410 may use optical scanning to identify a device (using object recognition or text recognition capabilities). Device ID module 410 may receive a video, image, a series of images, etc., from cameras 112. The video or images may include the medical device. Device ID module 410 may then use object recognition to identify the type of medical device depicted in the video or images. Device ID module 410 may also or alternatively use text recognition to identify text, a symbol, a label, or any other identifier on the medical device, and use the identification to identify the medical device.

In one embodiment, device ID module 410 may identify the medical device via a bar code. For example, a bar code may be recognized by device ID module 410, a sensor 304 may be configured to scan a bar code of the medical device, or otherwise. Device ID module 410 may then identify the medical device based on the bar code.

In one embodiment, each medical device may include a unique device identifier (e.g., each medical device may be numbered in a way that allows for easy inventory tracking). Device ID module 410 may be configured to identify each medical device by its unique device identifier, in addition to identifying the type of medical device. The unique identifier may be stored on an RFID tag, indicated by a number or symbol on the medical device, or otherwise.

Memory 406 is shown to include a device information module 412. Device information module 412 is configured to provide medical device support for an identified medical device. Device information module 412 may provide medical device properties, a preferred usage of the medical device, a supplier or manufacturer of the medical device, or a product specialist associated with the medical device. Device information module 412 may retrieve medical device information stored in medical device information database 428 or another source.

In one embodiment, the information relating to the individual medical device includes one or more product specialists associated with the medical device. The product specialist may be a designated person trained to provide medical support for use of the medical device. The product specialist information may be provided to video module 418 for setting up a teleconference with the product specialist.

In one embodiment, device information module 412 may be used to verify if the medical device is to be used in an operation. For example, device information module 412 may retrieve operation information from a patient information database 430. Patient information database 430 may store information relating to patients and operations to be performed on the patients. Device information module 412 may verify that the detected medical device should be used in the operation for the patient (e.g., if the right implant is selected for insertion, if the right tools are on hand for the operation, etc.).

In one embodiment, device information module 412 may provide training materials related to the medical device. The training materials may be information specific to the medical device (e.g., how to install an implant in a patient, how to use a particular tool, warnings, etc.). Device information module 412 may provide such training materials to the surgeons in the operating room when the medical device is detected. Regardless of a hospital and its staff's attempt to anticipate usage of medical devices in individual situations, it is usually not possible to account for every possible situation. Device information module 412 may be configured to provide such specific support for individual operations.

Memory 406 is shown to include a camera module 414. Camera module 414 is configured to control the operation of cameras 112 (and other recording devices) in an operating room 100. Camera module 414 may work in conjunction with other modules to support the activities of monitoring system 110. For example, camera module 414 may be configured to record video or images of a medical device for identification by device ID module 410. As another example, camera module 414 may be configured to record the usage of a medical device during an operation for a simulcast generated by video module 418.

Memory 406 is shown to include a display module 416. Display module 416 is configured to generate a user interface such as display 106 shown in FIG. 3. Display module 416 may work in conjunction with other modules to support the activities of monitoring system 110. For example, display module 416 may display device information from device information module 412, inventory information generated by inventory module 420, billing information generated by billing module 422, or information from patient information database 430. Display module 416 may display video of a product specialist 442 conducting a videoconference with a surgeon in operating room 100. Display module 416 may further generate a user interface that allows a user to manually enter information related to the medical device (e.g., to request a product specialist, to manually update inventory, to look up medical device information, etc.).

Memory 406 is shown to include a video module 418. Video module 418 is configured to set up a videoconference with a product specialist 442, set up a simulcast of operating room 100, or provide other video-related functions. Video module 418 may set up a link with a product specialist 442 identified by device information module 412.

In one embodiment, video module 418 may be configured to generate a conference including multiple product specialists. For example, an operation may include a plurality of medical devices, and each medical device may have a different product specialist. Monitoring system 110 may identify and contact each product specialist, and video module 418 may be configured to set up a conference such that the product specialists may collaborate with the surgeons in the operating room together.

Memory 406 generally includes inventory module 420, billing module 422, and ordering module 424 for providing sales services to the hospital. Modules 420-424 may generally be able to provide the same sales services an on-site product specialist normally provides. Modules 420-424 may automatically track inventory (instead of a product specialist manually tracking), create invoices for medical device use (instead of a product specialist manually generating the invoice), and generate orders for re-stocking the medical device (instead of a product specialist generating the order).

Memory 406 is shown to include an inventory module 420. Inventory module 420 is configured to track inventory of medical devices in a hospital. Inventory module 420 may, upon detection of a medical device by device ID module 410, update the inventory in the hospital (e.g., by indicating that the medical device is being used in an operation). Inventory module 420 may further provide obsolescence tracking (e.g., tracking when a medical device is not wanted or used). Inventory module 420 may further track an inventory history relating to the medical device. Inventory module 420 may update an inventory database 426. Inventory database 426 may be accessible by any computer system and may provide up-to-date information relating to the current stock of medical devices in the hospital, in the operating room, in a shipping container, or otherwise.

Memory 406 is shown to include a billing module 422. Billing module 422 is configured to generate an invoice for use of a medical device during an operation. For example, device ID module 410 may detect the usage of an implant in an operation. Billing module 422 may then generate an invoice charging the hospital for use of the implant. Billing module 422 may be configured to generate an invoice for each medical device, or may generate an invoice for the use of several medical devices over time.

Memory 406 is shown to include an ordering module 424. Ordering module 424 is configured to generate an order for one or more medical devices to provide to a vendor 440. In one embodiment, ordering module 424 may check inventory database 426 to determine the current stock of various medical devices in a hospital. If the stock of a particular medical device is running low or is out, ordering module 424 may be configured to automatically generate an order to replenish the stock of the medical device. In another embodiment, ordering module 424 may be configured to generate an order for one or more medical devices based on a user (e.g., surgeon) input. In another embodiment, ordering module 424 may be configured to provide a notification that an inventory of a medical device needs to be replenished.

In one embodiment, inventory module 420 and ordering module 424 may be configured to track usage of medical devices in a hospital. Inventory module 420 may track usage of medical devices in a hospital (as the inventory is updated), and ordering module 424 may be able to predict future usage of medical devices or develop a schedule for replacing a stock of medical devices in a hospital based on the usage. For example, when the stock of a medical device is reduced, ordering module 424 may predict when an order needs to be submitted to a vendor 440 so that the hospital does not run out of the medical device. Ordering module 424 may generate a medical device replacement schedule which allows for order generation on a scheduled basis.

Figure 5:
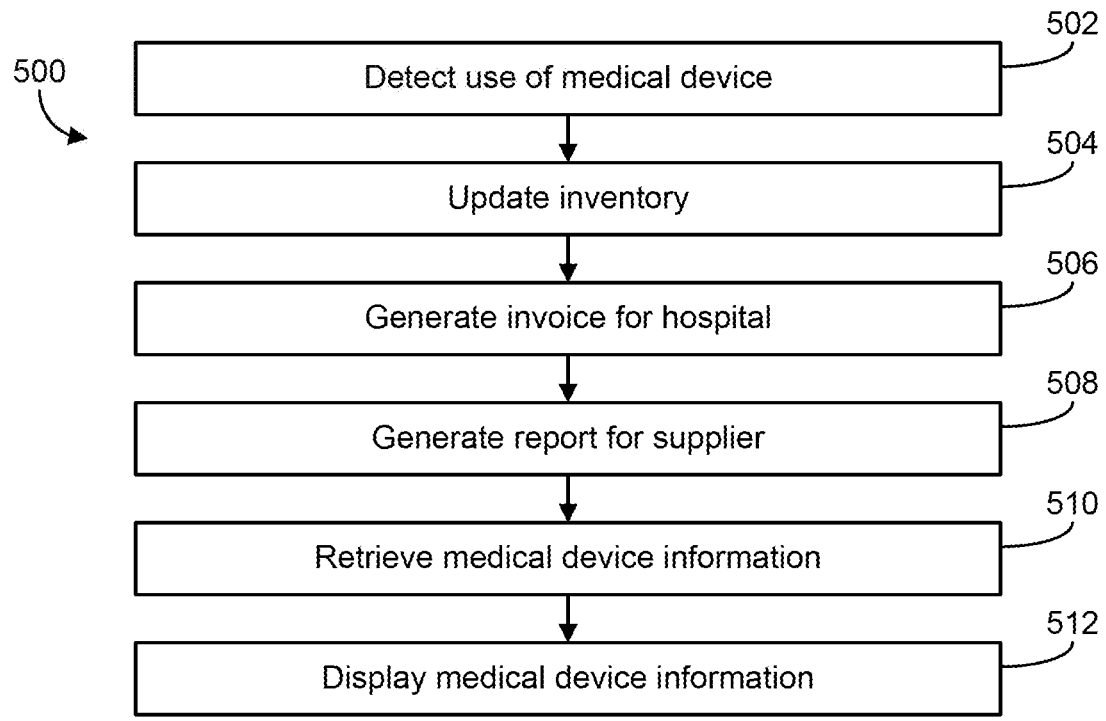
FIG. 5 is a flow chart of a process for providing various inventory and sales functions in response to a detected use of a medical device, according to an exemplary embodiment.

Referring to FIG. 5, a flow chart of a process 500 for providing various inventory and sales functions in response to a detected use of a medical device is shown, according to an exemplary embodiment. Process 500 may be executed by monitoring system 110 and more particularly modules 420-424 for providing services related to the medical device usage. Process 500 generally includes a detection step and several subsequent steps that may be executed based on the detection step. While process 500 illustrates several steps 504-512 in response to the detection of a medical device, it should be understood that some of steps 504-512 may not be executed, steps 504-512 may be executed in any order, or otherwise.

Process 500 includes detecting the use of the medical device (step 502). The use of the medical device may be detected in an operating room by a monitoring system. The medical device may include a RFID tag readable by a RFID reader, a bar code readable by a camera and monitoring system, or any other identifier configured to be readable by a monitoring system.

Process 500 includes updating an inventory of the medical device (step 504). Step 504 may generally include detecting the use of a medical device in an operation and updating the inventory in an inventory database as needed (e.g., if the medical device is implanted into a patient). Step 504 may further include detecting if a medical device is replaced or not used in an operation after an initial identification of the medical device.

Process 500 further includes generating an invoice for the hospital (step 506). The invoice charges the hospital for use of the medical device. In various embodiments, the invoice may be for use of a single medical device, or may be for the use of many medical devices, accumulated over time. Step 506 may include using current inventory information to determine when to generate the invoice. Step 506 may further include using other information (e.g., an invoice schedule, a particular date or time, etc.) to determine when to generate the invoice.

Process 500 further includes generating a report for a supplier (step 508). The report may generally relate to medical device usage in the hospital. For example, the report may indicate the current inventory in the hospital, outstanding invoices and other billing information related to the hospital, the operations the medical devices were used in, or otherwise. In various embodiments, reports may be generated on a scheduled basis or on a per-use basis. Step 508 may further include generating an order for more medical devices.

Process 500 further includes retrieving medical device information (step 510) and displaying the medical device information (step 512). For example, process 500 may be executed during an operation in an operating room. Steps 510-512 may include retrieving information relevant to the current operation and displaying the information on a monitor in the operating room in order to assist the surgeon in the operating room.

Figure 6:
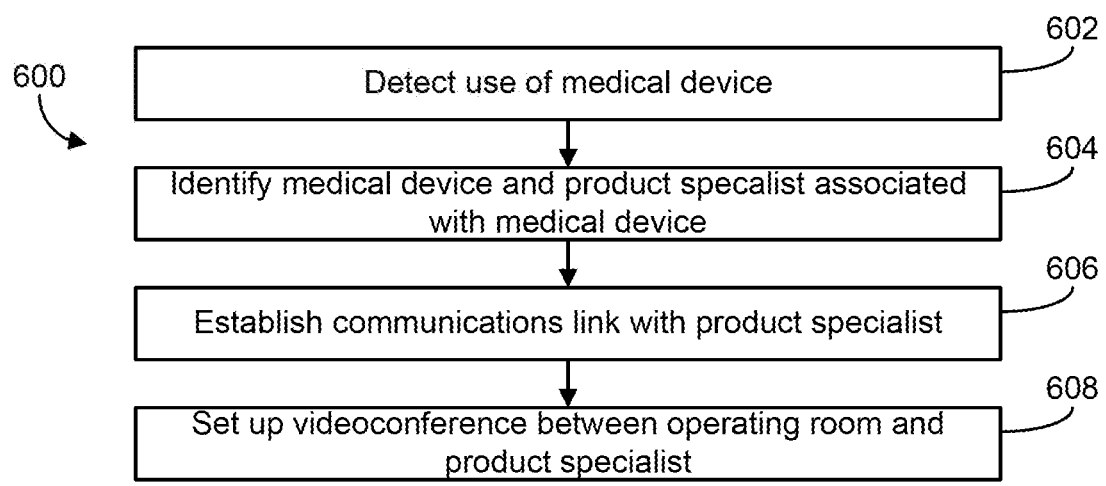
FIG. 6 is a flow chart of a process for providing a video connection between personnel in an operating room and a product specialist, according to an exemplary embodiment.

Referring to FIG. 6, a flow chart of a process 600 for providing a video connection between personnel in an operating room and a product specialist is shown, according to an exemplary embodiment. Process 600 may be executed by monitoring system 110 and more particularly modules 410-418 for providing services related to the medical device usage. Process 600 generally includes a detection step and several subsequent steps that may be executed based on the detection step. While process 600 illustrates several steps 604-608 in response to the detection of a medical device, it should be understood that some of steps 604-608 may not be executed, steps 604-608 may be executed in any order, or otherwise.

Process 600 includes detecting the use of a medical device (step 602). The use of the medical device may be detected in an operating room by a monitoring system. The medical device may include a RFID tag readable by a RFID reader, a bar code readable by a camera and monitoring system, or any other identifier configured to be readable by a monitoring system. Additionally or alternatively, step 602 may include a user request or other input relating to the medical device (e.g., a request for help relating to the medical device).

Process 600 includes identifying the medical device and a product specialist associated with the medical device (step 604). Step 604 may include identifying medical device information, a vendor or supplier of the medical device, and other information related to the medical device. The identification of such information may be made using a unique identifier of the medical device.

Process 600 includes establishing a communications link with the product specialist (step 606) and setting up a videoconference between the operating room and the product specialist (step 608). The product specialist may then provide advisory services to a surgeon for medical device usage, may monitor an operation, may provide live training for using the medical device, and provide other services "live" in the same manner that an on-site product specialist could.

Referring generally to FIGS. 1-6, a monitoring system is described that may be implemented in an operating room for tracking medical device usage. Alternatively or additionally, medical device usage may be tracked via shipping containers in which the medical devices are shipped to the hospital. A processing circuit integrated with the shipping container may be configured to track medical device usage by tracking when a medical device is removed from the shipping container. The processing circuit integrated with the shipping container may then provide various services relating to the medical device. For example, the processing circuit may be useful for sales (e.g., for ordering medical devices when the inventory runs low in the shipping container), inventory, quality control, obsolescence tracking (e.g., when a medical device is no longer usable), surgical training, and more.

Figure 7:
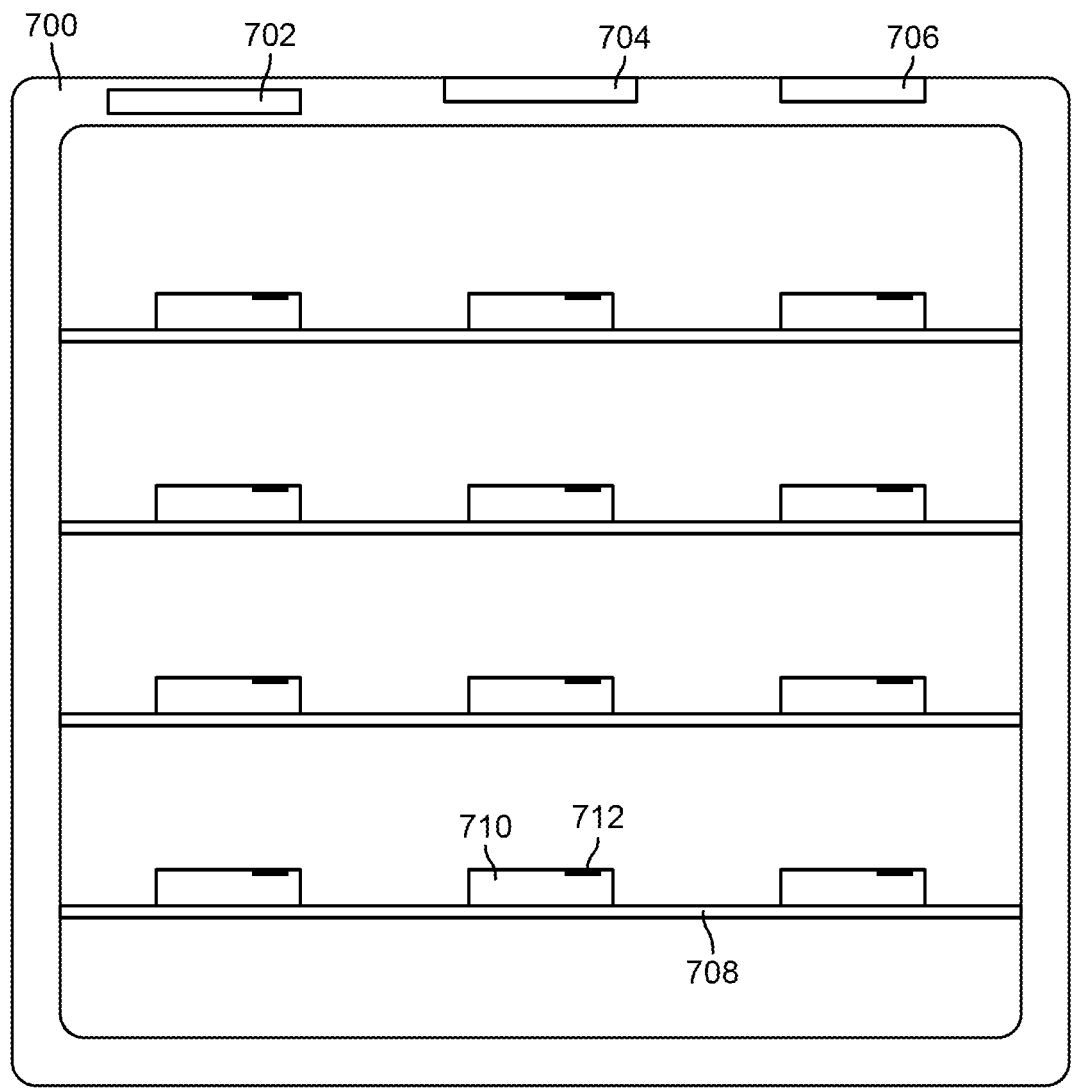
FIG. 7 is a perspective view of a shipping container including multiple trays and medical devices, according to an exemplary embodiment.

Referring now to FIG. 7, a shipping container 700 for medical devices is shown, according to an exemplary embodiment. Shipping container 700 includes a plurality of trays 708, each tray including one or more medical devices 710. Each medical device 710 may include an identifier 712. Each identifier 712 may be unique to its medical device 710. For example, each identifier may be numbered individually such that the individual device may be identified. As another example, identifiers 712 may be RFID tags with information unique to the medical device. Additionally, each tray 708 may include an identifier such as an RFID tag. The identifier for each tray 708 may include information relating to the individual contents of each tray.

As described above, the identifiers may be RFID tags. In one embodiment, the RFID tags may be a read/write tag that may be altered by the shipper before shipping container 700 is sent to a hospital, and may be altered by shipping container 700 when medical devices are removed. In another embodiment, the RFID tags may be a read-only tag to be replaced in shipping container 700 before each shipment.

Shipping container 700 is further shown to include a tracking system 702 configured to support the tracking activities of shipping container 700. Shipping container 700 further includes a display 704 on which medical device information may be displayed. Display 704 may include a monitor, lights, or any other type of display that provides information to a user relating to a current status of the content of shipping container 700. For example, display 704 may provide information relating to the removal of a medical device when the removal occurs. Shipping container 700 further includes an RFID reader 706 configured to read RFID tags. Shipping container 700 may alternatively or additionally include other sensors for tracking medical devices. While shipping container 700 illustrates a single RFID reader 706, in various embodiments, shipping container 700 may include any number of RFID readers.

Medical devices 710 may be shipped in shipping container 700 in one of two conditions. In one embodiment, each medical device may be sterilely packaged in a disposable or reusable container. The sterile packaging may contain individual RFID chips and/or visual identifiers such as a bar code or number. RFID reader 706 may be configured to detect each medical device 710 using the RFID chips, while a surgeon or other user may verify the correct medical device was chosen based on the visual identifier. In another embodiment, each medical device may be delivered in a tray 708 suitable for steam or gas sterilization. Each tray may be positioned such that the removal of the tray or any of its medical devices is automatically detected by RFID reader 706.

RFID reader 706 may detect the removal of one or more medical devices 710. Trays 708 and medical devices 710 may be positioned in shipping container 700 in such a way that the removal of a medical device 710 results in the detection of an identifier 712 by RFID reader 706. Further, RFID reader 706 may be configured to detect an identifier associated with a tray 708 to determine the current contents of the tray. Upon detection of an RFID tag by RFID reader 706, a signal may be sent to tracking system 702 for updating the inventory of shipping container 700 and providing services related to the removed medical device 710. In one embodiment, RFID reader 706 may detect the addition of one or more medical devices 710 to shipping container 700 as well.

Figure 8:
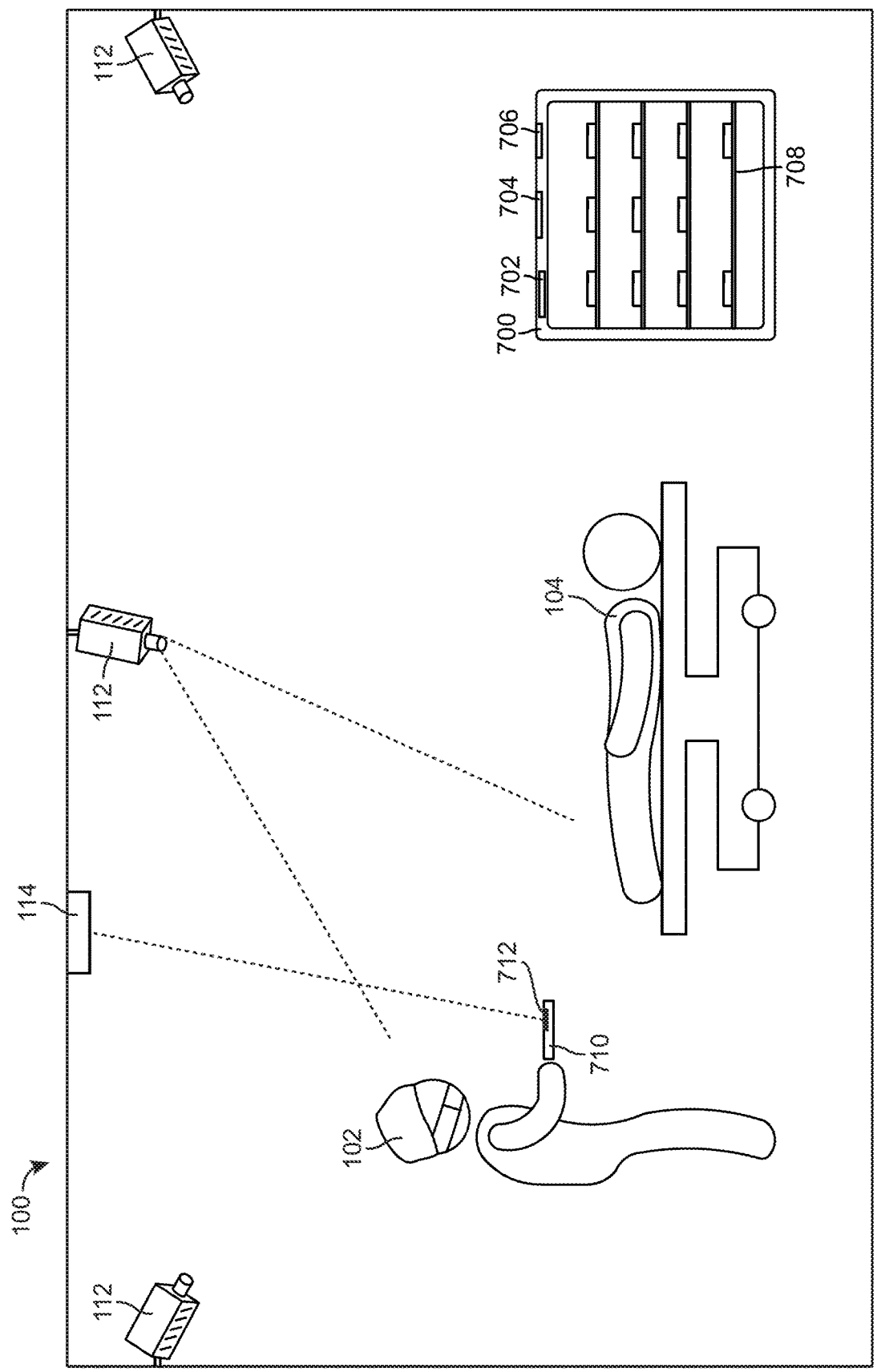
FIG. 8 is an illustration of an operating room, including the shipping container of FIG. 7 and cameras and sensors for detecting a medical device from the shipping container, according to an exemplary embodiment.

Referring also to FIG. 8, shipping container 700 is shown in operating room 100. In one embodiment, shipping container 700 may be located in operating room 100, and the tracking system of shipping container 700 may work in concert with monitoring system 110 of operating room 100. In another embodiment, shipping container 700 may be located remotely from operating room 100, but the tracking system of shipping container 700 may still work in concert with monitoring system 110. In yet another embodiment, the tracking system of shipping container 700 may operate independent of monitoring system 110.

In the embodiment of FIG. 8, a surgeon 102 removes a medical device 710 from shipping container 700. RFID reader 706 may detect the removal of medical device 710 via identifier 712 and may provide a signal to tracking system 702. Further, cameras 112 and/or RFID reader 114 of operating room 100 may also detect medical device 710 via identifier 712 or other identification methods. Tracking system 702 may be connected to cameras 112 and RFID reader 114 and verify the usage of medical device 710. Alternatively, a monitoring system 110 may verify the use, or monitoring system 110 and tracking system 702 may verify the detection with one another.

Figure 9:
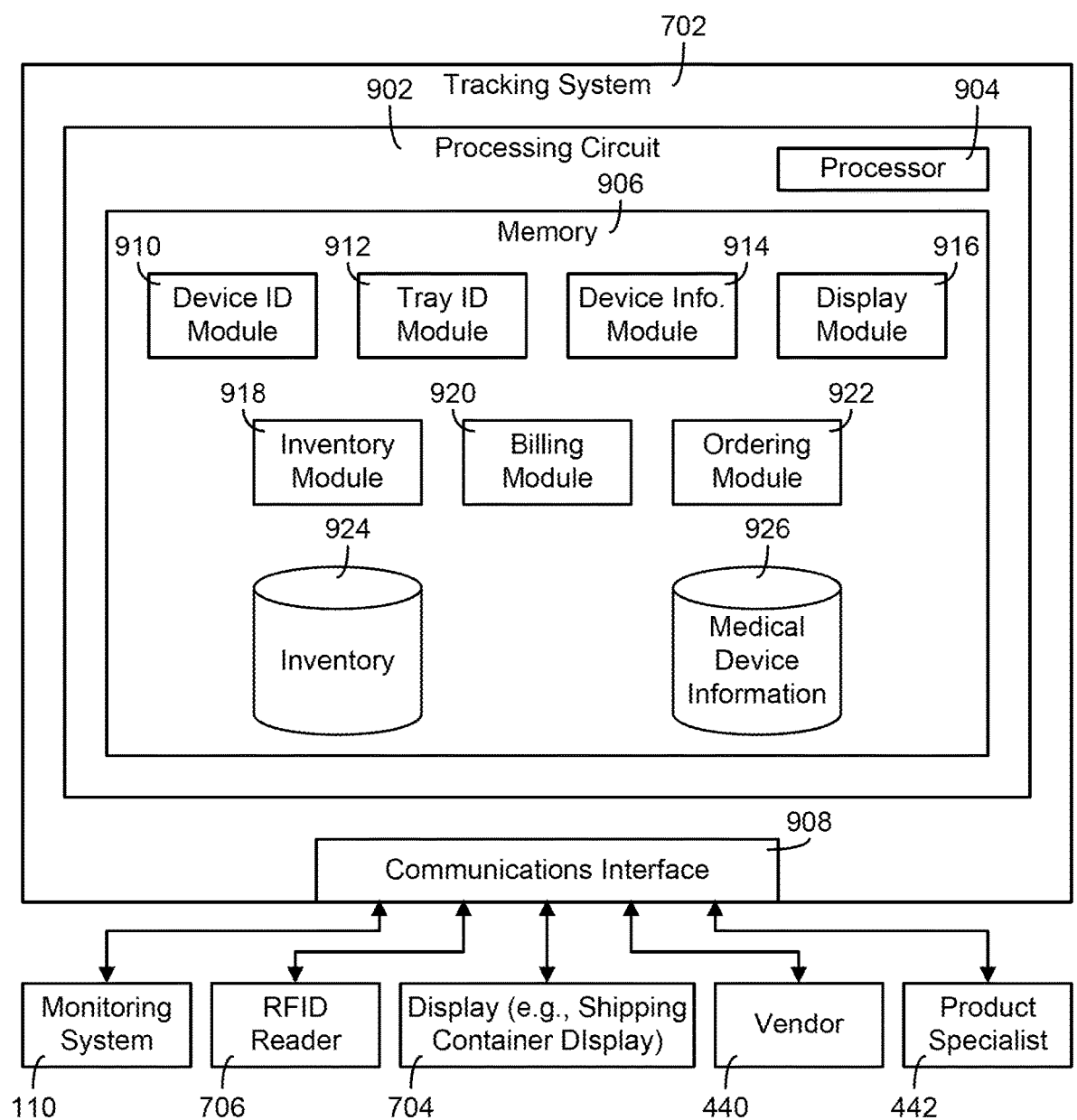
FIG. 9 is a block diagram of a tracking system integrated into the shipping container of FIG. 7 for tracking medical devices, according to an exemplary embodiment.

Referring now to FIG. 9, a tracking system 702 integrated with shipping container 700 is shown, according to an exemplary embodiment. Tracking system 702 may generally be configured to monitor activity related to shipping container 700, including the removal and use of one or more medical devices 710. For example, tracking system 702 may update inventory, identify a medical device 710 being removed and used, identify a product specialist associated with the removed medical device 710, and such services.

As shown in FIG. 7, tracking system 702 may be implemented as part of a computing system integrated with shipping container 700; in other embodiments, tracking system 702 may be implemented remotely from shipping container 700. Further, while tracking system is shown as a single system, it should be understood that some of the modules, databases, and other components of tracking system 702 may be located in different locations, computing devices, etc. (e.g., in monitoring system 110).

Tracking system 702 is shown in FIG. 7 as a system that may provide the services described in the present disclosure independently. In other embodiments, tracking system 702 may work in concert with monitoring system 110, or may provide some of the same functionality as monitoring system 110.

Tracking system 702 includes a processing circuit 902 including a processor 904 and memory 906. Tracking system 702 further includes a communications interface 908 configured to communicate with communicate with various equipment, devices, and the like. Communications interface 908 may be configured to establish a wireless or wired (e.g., USB) connection with any number of local devices (e.g., display 704, RFID reader 706), remote systems (e.g., monitoring system 110) or outside sources (e.g., vendor 440, product specialist 442, etc.). Processing circuit 902, processor 904, memory 906, and communications interface 908 may have the same general functionality as described above with reference to FIG. 4.

While communications interface 908 is shown connected to a plurality of devices and sources, communications interface 908 may further be connected to remote displays 106, remote devices 108, or other devices. If tracking system 702 is configured to control a simulcast or videoconference with an off-site product specialist, communications interface 908 may be configured to establish a wireless communications link with displays 106, remote devices 108, cameras 112, or RFID reader 114.

Memory 906 is shown to include a device ID module 910. Device ID module 910 is configured to identify a medical device based on a signal from RFID reader 706. RFID reader 706 may detect a medical device via an RFID tag on the medical device as the medical device is removed from shipping container 700. In one embodiment, each medical device may include a unique RFID tag. Device ID module 410 may be configured to identify each medical device by its unique RFID tag. In another embodiment, device ID module 910 may be configured to identify a medical device based on an input from another sensor, camera, etc., using object recognition or text recognition.

Memory 906 is shown to include a tray ID module 912. Tray ID module 912 is configured to identify a tray 708 in shipping container 700 via an RFID tag (or other identifier). Tray ID module 912 may use the RFID tag to determine the current contents of tray 708. Tray ID module 912 may further write information to an RFID tag of a tray 708. For example, if the contents of a tray are changed (e.g., a medical device is removed from the tray), tray ID module 912 may be configured to receive a signal from RFID reader 706 related to the removal of the medical device. Tray ID module 912 may then cause information stored on the RFID tag of the tray to be updated (e.g., the inventory of the tray). Similarly, if a medical device is placed on a tray, the signal may be sent to tray ID module 912 and the information on the RFID tag of the tray may be updated.

Memory 906 is shown to include device information module 914. Device information module 914 is configured to provide medical device support for a removed medical device. Device information module 914 may identify medical device properties, preferred usage of the medical device, or supplier or product specialist information associated with the medical device. Device information module 914 may pull information from an inventory database 924 or medical device information database 926. Inventory database 924 may store current inventory information for the shipping container. Medical device information database 926 may store information such as an associated vendor and product specialist for each medical device.

In one embodiment, the information relating to the individual medical device includes one or more product specialists associated with the medical device. The product specialist may be a designated person trained to provide medical support for use of the medical device. The product specialist information may be used to contact the product specialist for setting up a teleconference with the product specialist on a remote display.

In one embodiment, device information module 914 may be used to verify if the medical device is to be used in an operation. For example, device information module 914 may retrieve operation information and use the information to verify that the correct medical device was removed from shipping container 700. If the wrong medical device was taken, display 704 may display the information, or the information may be sent to a remote display.

Memory 906 is shown to include a display module 916. Display module 916 may be configured to control a display 704 associated with shipping container 700. In one embodiment, display 704 may be a display integrated with shipping container 700. In other embodiments, display 704 may be a display detachable from shipping container 700, may be a display located near shipping container 700, or may be a remote display configured to display information for one or more shipping containers. Display module 916 may be configured to generate a display providing inventory information, medical device information, and other information generated by the modules of tracking system 702.

While not shown in FIG. 9, memory 906 may additionally include a camera module and/or video module for controlling cameras and other equipment located remotely from tracking system 702. For example, if an operating room includes tracking system 702 and not an independent monitoring system 110, tracking system 702 may include the camera module and/or video module as described in FIG. 4 to control the operation of the cameras and to provide telecommunications with an off-site product specialist.

Memory 906 generally includes inventory module 918, billing module 920, and ordering module 922 for providing sales services to the hospital. Modules 918-922 may generally be able to provide the same sales services an on-site product specialist can. Modules 918-922 may automatically track inventory (instead of a product specialist manually tracking), create invoices for medical device use (instead of a product specialist manually generated invoice), and generate orders for re-stocking the medical device (instead of a product specialist).

Memory 906 is shown to include an inventory module 918. Inventory module 918 is configured to track inventory of shipping container 700. Inventory module 918 may, upon detection of removal of a medical device, update the inventory in inventory database 924. Inventory database 924 may be accessible by any computer system and may provide up-to-date information relating to the current stock of medical devices in the hospital to any number of systems. For example, inventory module 918 may provide inventory information upon arrival of shipping container 700 to a hospital or vendor.

Memory 406 is shown to include a billing module 920. Billing module 920 is configured to generate an invoice for use of a medical device. For example, billing module 920 may be configured to generate an invoice charging the hospital for use of a medical device when the medical device is removed from shipping container 700. Billing module 920 may be configured to wait for confirmation of use of the medical device before generating the invoice. Alternatively, billing module 920 may be configured to generate an invoice for more than one medical devices, for all medical devices in shipping container 700, or otherwise.

Memory 406 is shown to include an ordering module 922. Ordering module 922 is configured to generate an order for one or more medical devices to provide to a vendor 440. In one embodiment, ordering module 922 may check inventory database 924 to determine the current stock of medical devices in shipping container 700. If the stock is low or out in shipping container 700, ordering module 922 may be configured to automatically generate an order to provide to vendor 440 to replenish the stock of the medical device. In one embodiment, ordering module 922 may use a medical device usage rate, an estimated shipping time, or any other information that may impact the availability of medical devices in the hospital to determine when to generate an order.

In one embodiment, ordering module 922 may use inventory information from other shipping containers or other hospital inventory information (e.g., inventory database 426 of monitoring system 110) to determine the current stock of a medical device. Ordering module 922 may be configured to use all such inventory information to determine if and when an order should be generated. In another embodiment, ordering module 922 may be configured to provide a notification that an inventory of a medical device needs to be replenished before generating an order.

Figure 10:
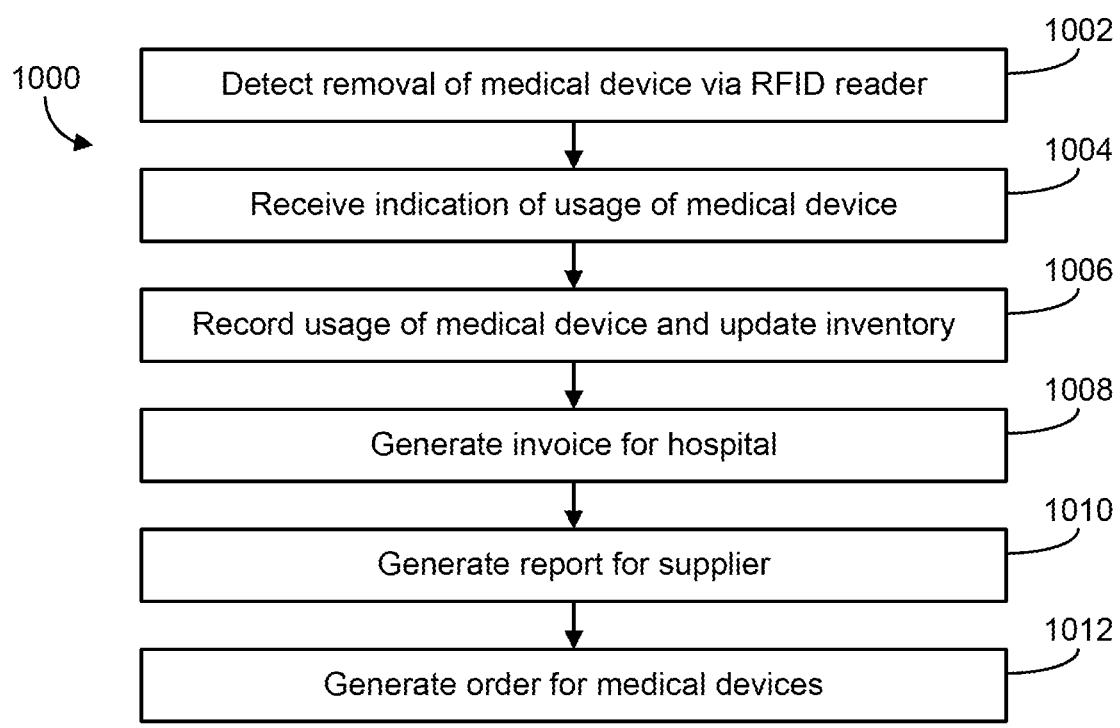
FIG. 10 is a flow chart of a process for tracking medical device usage of a medical device removed from a shipping container, according to an exemplary embodiment.

Referring to FIG. 10, a flow chart of a process 1000 for tracking medical device usage using a processing circuit of the shipping container is shown, according to an exemplary embodiment. Process 1000 may be executed by tracking system 702 and more particularly modules 910-922 for providing services related to the medical device usage. Process 1000 generally includes a detection step and several subsequent steps that may be executed based on the detection step. While process 1000 illustrates several steps 1006-1012 in response to the detection of a medical device, it should be understood that some of steps 1006-1012 may not be executed, steps 1006-1012 may be executed in any order, or otherwise.

Process 1000 includes detecting the removal of the medical device from the shipping container (step 1002). The detection of the medical device may be achieved via a RFID reader or other sensor integrated with the shipping container. Process 1000 may further include receiving an indication of usage of the medical device (step 1004). Such an indication may be received from a monitoring system, for example. In another embodiment, step 1004 may be skipped and steps 1006-1012 may be executed upon detection of removal of the medical device at step 1002.

Process 1000 includes recording usage of the medical device and updating an inventory of the shipping container (step 1006). Step 1006 may generally include updating an inventory database of the shipping container. Step 1006 may further include updating an overall inventory of the medical device in the hospital.

Process 1000 further includes generating an invoice for the hospital (step 1008). The invoice charges the hospital for use of the medical device. In various embodiments, the invoice may be for use of a single medical device, or may be for the use of many medical devices, accumulated over time. Step 1008 may include using current inventory information of the shipping container to determine when to generate the invoice. Step 506 may further include using other information (e.g., an invoice schedule, a particular date or time, etc.) to determine when to generate the invoice.

Process 1000 further includes generating a report for a supplier (step 1010). The report may generally relate to medical device usage in the hospital. For example, the report may indicate the current inventory in the shipping container, outstanding invoices and other billing information related to the shipping container, or otherwise. In various embodiments, reports may be generated on a scheduled basis or on a per-use basis.

Process 1000 further includes generating an order for medical devices for a supplier (step 1012). The order may replenish the stock of the medical device in the hospital. In one embodiment, the order may be generated when the shipping container is out of medical devices or reaches a minimum threshold of medical devices.

As described above, monitoring system 110 and/or tracking system 702 may provide various medical device-related services for a hospital. In one embodiment, a plurality of tracking systems for each shipping container in a hospital may be used to provide the features described herein. Any combination of monitoring systems and tracking systems (including the omission of a monitoring system or tracking system) may be used to provide the features described herein.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. Other substitutions, modifications, changes, and omissions may be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, networked systems or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions. The machine-executable instructions may be executed on any type of computing device (e.g., computer, laptop, etc.) or may be embedded on any type of electronic device (e.g., a portable storage device such as a flash drive, etc.).

Although the figures may show a specific order of method steps, the order of the steps may differ from what is depicted. Also, two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. An operating room display system comprising:
a display device;
a sensor coupled to the display device and configured to detect a presence of a medical device disposed within the operating room;
a communications interface communicatively coupled to the display device and the sensor; and
a memory communicably coupled to the communications interface and the sensor, the memory being configured to receive a signal from the sensor responsive to the sensor detecting the presence of the medical device;
wherein the display device, responsive to the memory receiving the signal, is configured to show a display providing information retrieved from the memory associated with the medical device, to a user in the operating room regarding the medical device detected by the sensor.

2. The operating room display system of claim 1, wherein the communications interface is configured to provide the display of the display device to a remote device.

3. The operating room display system of claim 1, wherein the memory is further configured to identify the device detected by the sensor.

4. The operating room display system of claim 1, wherein the display includes a video section configured to show a tutorial or instructions associated with use of the medical device.

5. The operating room display system of claim 1, wherein the display includes a training section.

6. The operating room display system of claim 5, wherein the training section is configured to show training materials associated with the medical device, wherein the training materials are retrieved from the memory.

7. The operating room display system of claim 6, wherein the training materials include at least one of installation instructions, use instructions, or warnings associated with the medical device.

8. The operating room display system of claim 5, wherein the training section is configured to show training material in response to the sensor detecting the medical device.

9. The operating room display system of claim 1, wherein the display includes a video section and a training section.

10. The operating room display system of claim 1, further comprising a camera positioned in the operating room.

11. The operating room display system of claim 10, wherein the communications interface is configured to enable communication between an individual outside the operating room and the user using the display device and the camera.

12. The operating room display system of claim 11, wherein the individual outside the operating room is a product specialist associated with the medical device.

13. An operating room display system comprising:
a display device;
a camera coupled to the display device;
a communications interface communicatively coupled to the display device and the camera; and
a memory communicably coupled to the communications interface and the camera, the memory being configured to control operation of the camera and the display device;
wherein the display device is configured to show a display having a video portion to enable video communication between an individual outside the operating room and a user in the operating room using the display device and the camera as controlled by the memory.

14. The operating room display system of claim 13, wherein the video portion is configured to show a live stream communication from the individual outside the operating room.

15. The operating room display system of claim 13, wherein the communications interface is configured to allow remote viewing of the operating room using the camera.

16. The operating room display system of claim 13, wherein the communications interface is configured to provide at least a portion of the display of the display device to one or more remote devices.

17. A method for providing a display in an operating room comprising:
  detecting, by a sensor, a presence of a medical device within the operating room;
  retrieving, by a processor in communication with the sensor, information associated with the medical device from a memory in response to receiving a signal from the sensor indicating detection of the presence of the medical device; and
  causing, by the processor, the information to be shown on a display of a display device coupled to the sensor and the processor responsive to processor retrieving the information;
  wherein the display of the display device includes at least one of a video portion and a training portion.

18. The method of claim 17, further comprising showing a tutorial or instructions associated with use of the medical device on the video portion of the display.

19. The method of claim 17, further comprising showing training materials associated with the medical device on the training portion of the display.

20. The method of claim 17, further comprising providing the display of the display device to a remote device.

* * * * *